United States Patent [19]

Ravichandran et al.

[11] Patent Number: 4,898,901

[45] Date of Patent: Feb. 6, 1990

[54] LONG CHAIN N-ALKYL-ALPHA-ALKYL NITRONES AND POLYOLEFIN COMPOSITIONS STABILIZED THEREWITH

[75] Inventors: Ramanathan Ravichandran, Yonkers, N.Y.; Stephen D. Pastor, Basel, Switzerland; Raymond Seltzer, New City, N.Y.; Ambelal R. Patel, Ardsley, N.Y.

[73] Assignee: Ciba-Geigy Corporation, Ardsley, N.Y.

[21] Appl. No.: 330,986

[22] Filed: Mar. 23, 1989

Related U.S. Application Data

[63] Continuation of Ser. No. 105,417, Oct. 7, 1987, abandoned.

[51] Int. Cl.[4] .................... C07C 135/00; C08K 5/32
[52] U.S. Cl. ................................ 524/237; 524/101; 524/291; 524/343; 524/236; 524/237; 564/248; 564/300; 564/301
[58] Field of Search .............. 564/300, 301, 248; 524/237

[56] References Cited

U.S. PATENT DOCUMENTS 3,894,085  7/1975  Eschenmoser ................ 564/248
3,917,700  11/1975  Auerbach ..................... 260/566 R
3,950,327  4/1976  Eschenmoser ................ 564/276
4,596,874  6/1986  Murahashi et al. ............ 564/248
4,709,107  11/1987  West et al. ................... 564/301

FOREIGN PATENT DOCUMENTS 59-11345  1/1984  Japan .
2137619  3/1984  United Kingdom .

OTHER PUBLICATIONS

K. B. Chakraborty et al: J. Applied Polymer Science, 30; 3267–3281 (1985).
CA 106:4388n (1987).
CA 105:173628e (1986).
L. P. Nethsinghe et al.: Rubber Chemistry and Technology, 57 pp. 779–791 (1984)
M. Schulz et al.: Plaste Kautsch, 209 (1986) A. Y. Gerchikov et al.: Zh Prikl. Khim.; 1082 (1986).

Primary Examiner—Veronica P. Hoke
Attorney, Agent, or Firm—Luther A. R. Hall

[57] ABSTRACT

Long chain N-alkyl-alpha-alkyl nitrones represent particularly valuable process stabilizers for polyolefin compositions. The nitrone derived from the long chain alkyl mixture present in di(hydrogenated tallow)amine is especially useful for this purpose.

28 Claims, No Drawings

LONG CHAIN N-ALKYL-ALPHA-ALKYL NITRONES AND POLYOLEFIN COMPOSITIONS STABILIZED THEREWITH

This is a continuation of application Ser. No. 105,417, filed on Oct. 7, 1987, now abandoned.

This invention pertains to novel long chain N-alkyl-alpha-alkyl nitrones and to polyolefin compositions stabilized with such nitrones.

BACKGROUND OF THE INVENTION

L. P. Nethsinghe et al, Rubber Chem. Tech. 57, 779 (1984) show that N-lower alkyl-alpha-phenyl or substituted phenyl nitrones are effective antifatigue, antioxidant and antiozonant agents for vulcanized rubber.

K. B. Chakraborty et al, J. Appl. Poly. Sci., 30, 3267 (1985) disclose aldonitrones containing a phenolic group which are effective as melt stabilizers for polypropylene. These nitrones are the N-phenyl or N-tert-butyl-alpha phenyl or substituted phenyl nitrones.

A. Y. Gerchikov et al, Zh. Prikl. Khim., 1986, 108 (C.A., 106, 4388n (1987)) describe amide substituted nitrones as antioxidants for industrial esters derived from pentaerythritol.

Japanese Sho No. 59-11345 describes the melt stabilization of olefin polymers using selected aldonitrones and ketonitrones. N-tert-butyl-alpha-phenyl nitrone is exemplified as a process stabilizer for polypropylene. Substitution on the N-atom of the nitrone is described as alkyl of 1 to 18 carbon atoms, phenyl or tolyl. Substitution on the alpha-carbon is hydrogen, phenyl or substituted phenyl.

M. Schulz et al, Plaste Kautsch. 1986, 209 (C.A. 105, 173628a (1986)) discloses the antioxidant activity of N-phenyl aldonitrones or ketonitrones as antioxidant activity of N-phenyl aldonitrones or ketonitrones as antioxidants for polypropylene. N-tert-butyl or N-phenyl-alpha-phenyl or substituted phenyl nitrones are described.

None of these references disclose the instant long chain N-alkyl-alpha-alkyl nitrones or their use as process stabilizers for polyolefins.

OBJECTS OF THE INVENTION

One object of the instant invention is to provide long chain N-alkyl-alpha-alkyl nitrones which are useful as excellent process stabilizers for polyolefin compositions.

Another object of this invention is to provide stabilized polyolefin compositions containing as process stabilizers the long chain N-alkyl-alpha-alkyl nitrones.

DETAILED DISCLOSURE

The instant invention pertains to long chain N-alkyl-alpha-alkyl nitrones which are exceptionally effective as process stabilizers for polyolefins.

The instant nitrones are of the formula

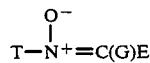

wherein
T is a straight or branched chain alkyl of 8 to 18 carbon atoms,
G is hydrogen, methyl or ethyl,
E is a straight or branched chain alkyl of 5 to 17 carbon atoms, and
where the sum of the carbon atoms in G plus E is equal to 7 to 17.

Preferably T is n-octyl, n-decyl, dodecyl, tetradecyl, hexadecyl, heptadecyl or octadecyl. Most preferably T is the alkyl mixture found in hydrogenated tallow amine.

Preferably G is hydrogen or methyl. Most preferably G is hydrogen.

Preferably E is n-heptyl, n-nonyl, undecyl, tridecyl, pentadecyl, hexadecyl or heptadecyl. Most preferably E is the alkyl mixture found in hydrogenated tallow amine with one less carbon atom per alkyl group.

A typical di(hydrogenated tallow)amine has the following distribution of alkyl substituents:

| | $L_1L_2NH$ | |
|---|---|---|
| $L_1$ | $L_2$ | % |
| $C_{16}$ | $C_{14}$ | 1.9 |
| $C_{16}$ | $C_{16}$ | 12.4 |
| $C_{16}$ | $C_{17}$ | 2.8 |
| $C_{16}$ | $C_{18}$ | 36.0 |
| $C_{17}$ | $C_{18}$ | 3.9 |
| $C_{18}$ | $C_{18}$ | 39.0 |
| other | | 4.0 |

It is clear that the di(hydrogenated tallow)amine originating from animal sources may well vary somewhat in the specific distribution of alkyl substituents, but the di(hydrogenated tallow)amine contains major amounts of N,N-dihexadecylamine, N,N-dioctadecylamine and N-hexadecyl-N-octadecylamine. The individual components of the mixture can be separated by distillation under high vacuum.

However, for the purposes of this invention, there is no need to carry out such separation. Indeed, the di(hydrogenated tallow)amine represents a preferred starting material for preparing the instant nitrones.

The instant nitrones can be prepared by a number of methods. These include (a) reaction of a long chain alkyl aldehyde or ketone with a long chain N-alkylhydroxylamine; or (b) the oxidation of a long chain N,N-dialkylamine or a long chain N,N-dialkylhydroxylamine with any classic oxidizing agent. Suitable oxidizing agents include aqueous hydrogen peroxide, benzoyl peroxide, tert-butyl hydroperoxide, cumene hydroperoxide and 3-chloroperoxybenzoic acid.

The intermediates used for these synthetic methods are largely items of commerce.

Some selected nitrones have been shown to have some stabilizing effects on polymer substrates such as rubber or polyolefins as the earlier cited prior art references attest.

However, the stabilization of polymers which are processed at elevated temperatures remains a serious practical problem. This is typified by the processing of polyolefins such as polyethylene and polypropylene.

The instant invention also pertains to stabilized compositions which comprise
(a) a saturated polyolefin or mixture thereof, and
(b) a stabilizing amount of a long chain N-alkyl-alpha-alkyl nitrone of the formula

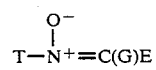

wherein

T is a straight or branched chain alkyl of 8 to 18 carbon atoms,

G is hydrogen, methyl or ethyl,

E is a straight or branched chain alkyl of 5 to 17 carbon atoms, and where the sum of the carbon atoms in G plus E is equal to 7 to 17.

The instant nitrones are described in detail above. The most preferred long chain alkyl in the definitions of T and E is the alkyl mixture found in hydrogenated tallow amine.

The polyolefin of the instant compositions is a homopolymer or copolymer of an alpha-olefin.

The saturated polyolefins useful in the instant compositions are the polymers derived from monoolefins, such as polyethylene, which can be crosslinked, polypropylene, polyisobutylene, polybutene-1, poly-3-methylbutene-1 and poly-4-methylpentene-1. Polyethylene may be for example medium density, high density or linear low density polyethylene.

Mixtures of the homopolymers cited above, for example mixtures of polypropylene and polyethylene, polypropylene and polybutene-1, or polypropylene and polyisobutylene and the like, may also be used.

Copolymers of monoolefins may also be used in the instant compositions, for example ethylene/propylene copolymers, propylene/butene-1 copolymers, propylene/octene-1 copolymers, ethylene/butene-1 copolymers, ethylene/octene-1 copolymers as well as ethylene/vinyl acetate copolymers.

The instant compositions particularly employ as the polyolefin component polyethylene, polypropylene, polyisobutylene, poly(butene-1), poly(pentene-1), poly(3-methylbutene-1), poly(4-methylpentene-1) and various ethylene and propylene copolymers.

Especially preferred polyolefin substrates are polypropylene, low density polyethylene, medium density polyethylene, high density polyethylene, linear low density polyethylene, poly(butene-1), ethylene/vinyl acetate copolymer, ethylene/propylene copolymer and copolymers of ethylene or of propylene with higher alpha olefins.

The most preferred polyolefin substrate polypropylene, high density polyethylene, ethylene/propylene copolymer or a copolymer of ethylene or of propylene with another alpha olefin.

The polyolefins used in the food wrapping industry are of particular interest in these compositions.

The instant stabilized compositions may additionally contain a stabilizing amount of a stabilizer or mixture of stabilizers selected from the group consisting of the phenolic antioxidants, the hindered amine light stabilizers, the ultraviolet light absorbers, the organic phosphorus compounds, the alkaline metal salts of fatty acids, the thiosynergist and the hydroxylamines.

A particularly preferred embodiment of the instant invention is a stabilized composition which additionally contains (c) a stabilizing amount of an alkaline metal salt of a fatty acid or mixture thereof.

The alkaline metal salts of a fatty acid useful in the instant compositions are the alkali metal, alkaline earth metal, zinc, cadmium or aluminum salts of the higher fatty acids for example calcium stearate, zinc stearate, magnesium behanate, sodium ricinoleate or potassium palmitate. Calcium stearate or zinc stearate are particularly preferred.

Another preferred embodiment of the instant invention pertains to stabilized compostions which additionally contain (d) a stabilizing amount of a phenolic antioxidant or mixture thereof.

The phenolic antioxidants useful in such instant compositions embrace a large family of compounds examples of which are given below.

Antioxidants:

Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol 2,6-dioctadecyl-4-methylphenol and 2,6-di-tert-butyl-phenol.

Derivatives of alkylated hydroquinones, such as for example, 2,5-di-tert.-butyl-hydroquinone, 2,5-di-tert.-amylhydroquinone, 2,6-di-tert.-butyl-hydroquinone, 2,5-di-tert.-butyl-4-hydroxyanisole, 3,5-di-tert.-butyl-4-hydroxyanisole, tris-(3,5-di-tert.-butyl-4-hydroxyphenyl) phosphite, 3,5-di-tert.-butyl-4-hydroxyphenyl stearate and bis-(3,5-di-tert.-butyl-4-hydroxyphenyl) adipate.

Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.butyl-2-methylphenol) and 4,4'-bis-(2,6-dimethyl-4-hydroxy phenyl) disulfide.

Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butylphenol), 2,6-di(3-tert.-butyl-5-methyl-2-hydroxybenzyl)4-methylphenol, 2,2'-methylene-bis-[4-methyl-6-(alpha-methylcyclohexyl)-phenol], 1,1-bis(3,5-dimethyl-2-hydroxyphenyl)butane, 1,1-bis-(5-tert.-butyl-4-hydroxy-2-methylphenyl)butane, 2,2-bis-(3,5-di-tert.-butyl-4-hydroxyphenyl)propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)pentane and ethylene bis-[3,3-bis-(3-tert.-butyl-4-hydroxyphenyl)butyrate].

O-, N- and S-benzyl compounds, such as, for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.butyl-3-hydroxy-2,6-dimethylbenzyl) dithioterephthalate.

Hydroxybenzylated malonates, such as for example, dioctadecyl 2,2-bis-(3,5-di-tert.-butyl-2-hydroxybenzyl)malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)phenyl] 2,2-bis-(3,5-di-tert.-butyl-4-hydroxybenzyl)-malonate.

Hydroxybenzyl-aromatic compounds, such as, for example, 1,3,5-tri-(3,5-di-tert.-butyl-4-hydroxybenzyl)-2,4,6-tri-methylbenzene, 1,4-di-(3,5-di-tert.butyl-4-hydroxybenzyl)-2,3,5,6-tetramethylbenzene and 2,4,6-tri(3,5-di-tert.-butyl--hydroxybenzyl)-phenol.

s-Triazine compounds, such as, for example, 2,4-bis-octylmercapto-6-(3,5-di-tert.-butyl-4-hydroxy-anilino)-s-triazine, 2-octylmercapto-4,6-bis-(3,5-di-tert.-butyl-4-hydroxy-anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s- triazine, 1,3,5-tris-(2,6-dimethyl-3-hydroxy-4-tert.-butylbenzyl) isocyanurate and 1,3,5-tris-(3,5-di-tert.-butyl--hydroxybenzyl) isocyanurate.

Amides of β-(3,5-di-tert.-butyl-4-hydroxyphenyl)propionic acid, such as, for example, 1,3,5-tris-(3,5-di-tert.-butyl-4 hydroxyphenyl-propionyl)-hexahydro-s-triazine and N,N'-di(3,5-di-tert.-butyl-4-hydroxyphenyl-propionyl)-hexamethylene-diamine. N,N'-bis-β-(3,5-di-t-butyl-4-hydroxyphenyl)-propionyl-hydrazine.

Esters of β-(3,5-di-tert.-butyl-4-hydroxyphenyl)propionic acid with monohydric or polyhydric alcohols, such as, for example, with methanol, ethanol, octadecanol, 1,6-hexaenediol, 1,9-nonanediol, ethylene glycol, 1,2-propanediol, diethylene glycol, thiodiethylene glycol, triethylene glycol, neopentylglycol, pentaerythritol,-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2.2.2]octane.

Esters of β-(5-tert.-butyl-4-hydroxy-3-methylphenyl)propionic acid with monohydric or polyhydric alcohols, such as, for example, with methanol, ethanol, octadecanol, 1,6-hexane-diol, 1,9-nonanediol, ethylene glycol, 1,2-propanediol, diethylene glycol, triethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]octane.

Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propenediol, diethylene glycol, thio-diethylene glycol, neopentylglycol, pentaerythritol, 3-thia-undecanol, 3-thia-pentadecanol, trimethylhexanediol, trimethylolethane, trimethylolpropane, tris-hydroxyethyl isocynurate and 4-hydroxymethyl-1-phospha-2,6,7-trioxabicyclo[2.2.2]-octane, especially the tetrakis ester of pentaerythritol.

Benzylphosphonates, such as, for example, dimethyl 3,5-di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl tert.-butyl-4-hydroxy-3-methylbenzylphosphonate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3-tris(2-methyl-4-hydroxy-5-tert-butylphenyl)butane, 1,3,5-tris[2-(3,5-di-tertbutyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert.butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The stabilized polyolefin compositions of the instant invention may also contain other additives including the light stabilizers, ultraviolet light absorbers, organic phosphorus compounds, metal deactivators, pigments, colorants, dyes, talc and other fillers, and other conventional additives.

In general, the nitrone stabilizers of this invention are employed from about 0.01 to about 5% by weight of the stabilized composition, although this will vary with the particular substrate and application. An advantageous range is from about 0.025 to about 2%, and especially 0.05 to about 1%.

The nitrones of this invention stabilize polyolefins especially during high temperature processing with relatively little change in color and melt flow values even though the polymer may undergo a number of extrusions.

The instant compositions also contain from 0.01 to 2% of the alkaline metal salt of a fatty acid, preferably 0.05 to 1%, and especially 0.1 to 0.5% by weight of the stabilized composition.

The instant stabilizers may be readily incorporated into the polyolefins by conventional techniques at any convenient stage prior to the manufacture of shaped articles therefrom. For example, the stabilizer may be mixed with the polymer in dry powder form, or a suspension or emulsion of the stabilizer may be mixed with a solution, suspension or emulsion of the polymer. The stabilized polyolefin compositions of the invention may optionally also contain from about 0.01 to about 5%, preferably from about 0.025 to about 2%, and especially from about 0.1 to about 1% by weight of various conventional additives, such as the materials listed below, or mixtures thereof.

The following may be mentioned as examples of further additives that can be used in the instant compositions.

When the instant compositions contain an organic phosphorus compound, such compounds may be for example, triphenyl phosphite, diphenylalkyl phosphites, phenyldialkyl phosphites, tri-(nonylphenyl) phosphite, tri-lauryl phosphite, trioctadecyl phosphite, di(isodecyloxy)-2,4,8,10-tetraoxa-3,9-diphospha-[5.5]-undecane and tri-(4-hydroxy-3,5-di-tert.butylphenyl) phosphite or similar phosphonites.

The organic phosphorus compound of particular interest is selected from the group consisting of tris(2,4-di-tert-butylphenyl) phosphite, 3,9-di(2,4-di-tert-butylphenoxy)-2,4,8,10-tetraoxa-3,9-diphospha[5.5]undecane, tris(p-nonyl-phenyl) phosphite, 3,9-distearyloxy-2,4,8,10-tetraoxa-3,9-diphospha[5.5]undecane, dilauryl phosphite, 3,9-di[2,6-di-tert-butyl-4-(2-(n-octadecyloxycarbonyl)-ethyl)-phenoxy]-2,4,8,10-tetraoxa-3,9-diphospha[5.5]undecane and tetrakis(2,-4-di-tert-butylphenyl)4,4'-bis(diphenylene) phosphonite. Tris(2,4-di-tert-butylphenyl) phosphite is especially preferred.

When the instant compositions contain a thiosynergist, such thiosynergists may be for example dilauryl thiodipropionate, distearyl thiodipropionate or neopentanetetrayl tetrakis(3-dodecylthiopropionate). Distearyl thiodipropionate or dilauryl thiodipropionate is particularly preferred.

When the instant compositions contain a hindered amine light stabilizer, such hindered amines may for example be 4-benzoyl-2,2,6,6-tetramethylpiperidine, 4-stearyloxy-2,2,6,6-tetramethylpiperidine, bis-(2,2,6,6-tetramethylpiperidyl)sebacate or 3-n-octyl-7,7,9,9-tetramethyl-1,3,8-triaza-spiro[4.5]decane-2,4-dione.

The hindered amine light stabilizer of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, tris(2,2,6,6-tetramethylpiperidin-4-yl) nitrilotriacetate, 1,2-bis(2,2,6,6-tetramethyl-3-oxopiperazin n-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis(amino-2,2,6,6-tetramethylpiperidine) and 1,2-dibromoethane, polycondensation product of 2,4-dichloro-6-morpholino-s-triazine and 4,4'-hexamethylenebis(amino-2,2,6,6-tetramethylpiperidine), N,N'N'',N'''-tetrakis[(4,6-bis(butyl(2,2,6,6-tetramethyl-piperidin-4-yl)-amino-s-triazin-2-yl]-1,10-diamino-4,7-diazadecane, octamethylene bis(2,2,6,6-tetramethyl-piperidin-4-carboxylate) and 4,4'-ethylenebis(2,2,6,6-tetra-methylpiperazin-3-one).

A most preferred hindered amine light stabilizer is bis(2,2,6,6-tetramethylpiperidin-4-yl) sebacate, the polycondensation product of 1-(2-hydroxyethyl)-2,2,6,6-tetramethyl-4-hydroxypiperidine and succinic acid, the polycondensation product of 2,4-dichloro-6-tertoctylamino-s-triazine and 4,4'-hexamethylenebis-(amino-2,2,6,6-tetramethylpiperidine) or N,N',N'',N'''-tetrakis[(4,6-bis(butyl(2,2,6,6-tetramethyl-piperidin-4-yl)amino)-s-triazine-2-yl]-1,10-diamino-4,7-diazadecane.

When the instant compositions contain an ultraviolet light absorber, such light absorbers may include the 2H-benzotriazoles, the benzophenones, the oxanilides, the alpha-cyanocinnamates the substituted benzoate esters or the nickel salts of the O-alkyl hindered phenolic benzylphosphonates.

Examples of such ultraviolet light absorbers are seen below.

UV-Absorbers 2-(2'-Hydroxyphenyl)-benzotriazoles, e.g., the 5'-methyl-, 3',5'-di-tert.-butyl-, 5'-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-alpha-methyl-benzyl-5'-methyl, 3'-alphamethylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl-derivative.

2,4-bis(2'-Hydroxyphenyl)-6-alkyl-s-triazines, e.g., the 6-ethyl-, 6-heptadecyl- or 6-undecyl-derivative.

2-Hydroxybenzophenones e.g., the 4-hydroxy-, 4-methoxy-, 4-octoxy-, 4-decloxy-, 4-dodecyloxy-, 4-benzyloxy-, 4,2',4'-trihydroxy-, 2,2',4,4'-tetrahydroxy or 2'-hydroxy-4,4'-dimethoxy-derivative.

1,3-bis-(2'-Hydroxybenzoyl)-benzenes, e.g., 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'-dodeoyloxy-benzoyl)-benzene.

Esters of optionally substituted benzoic acids, e.g., phenyl salicylate, octylphenyl salicylate, dibenzoylresorcin, bis-(4-tert.-butylbenzoyl)-resorcin, benzoylresorcin, 3,5-di-tert.-butyl-4-hydroxybenzoic acid 2,4-di-tert.-butyl-phenyl ester or -2-octadecyl ester or 2-methyl-4,6-di-tert.-butyl ester.

Acrylates, e.g., alpha-cyano-$\beta$, $\beta$-diphenylacrylic acid-ethyl ester or isooctyl ester, alpha-carbomethoxy-cinnamic acid methyl ester, alpha-cyano-$\beta$-methyl-p-methoxycinnamic acid methyl ester or -butyl ester or N($\beta$-carbomethoxyvinyl)-2-methyl-indoline.

Oxalic acid diamides, e.g., 4,4'-di-octyloxy-oxanilide, 2,2'-di-octyloxy-5,5'-di-tert.-butyl-oxanilide, 2,2'-di-dodecyloxy-5,5'di-tert.-butyl-oxanilide, 2-ethoxy-2'-ethyl-oxanilide, N,N'-bis(3-dimethyl-aminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixtures of ortho- and para-methoxy- as well as of o- and p-ethoxy-disubstituted oxanilides.

Preferably the ultraviolet light absorber useful in the instant compositions is 2-(2-hydroxy-5-methylphenyl)-2H-benzotriazole, 2-(2-hydroxy-3,5-di-tert-amyl-phenyl)-2H-benzotriazole, 2-[2-hydroxy-3,5-di-(alpha,alpha-dimethylbenzyl)phenyl]-2H-benzotriazole, 2-(2-hydroxy-5-tert-octylphenyl)-2H-benzotriazole, 2-hydroxy-4-octyloxybenzophenone, nickel bis(O-ethyl 3,5-di-tert-butyl-4-hydroxybenzylphosphonate), 2,4-dihydroxybenzophenone, 2-(2-hydroxy-3-tert-butyl-5-methylphenyl)-2H-benzotriazole, nickel butylamine complex with 2,2'-thiobis(4-tert-butylphenol), 2-ethoxy-2'-ethyloxanilide or 2-ethoxy-2'-ethyl-5,5'-di-tert-butyloxanilide.

When the instant compositions contain a hydroxylamine such hydroxylamine may be for example an N,N-diaralkylhydroxylamine, an N,N-dicycloalkylhydroxylamine or an N,N-dialkylhydroxylamine. Preferred examples of such hydroxylamines include N,N-dibenzylhydroxylamine, substituted N,N-dibenzylhydroxylamines, N,N-dicyclohexylhydroxylamine and the N,N-dialkylhydroxylamines where alkyl is of 8 to 18 carbon atoms.

The following may be mentioned as examples of further additives that can be used in the instant compositions.

Metal deactivators, e.g., oxanilide, isophthalic acid dihydrazide, sebacic acid-bis-phenylhydrazide, bis-benzylidene-oxalic acid hydrazide, N,N'-diacetal-adipic acid dihydrazide, N,N'-bis salicyloyl-oxalic acid dihydrazide, N,N'-bis-salicyloyl-hydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

Nucleation agents, e.g., 4-tert.-butylbenzoic acid, adipic acid, diphenylacetic acid or substituted sorbitols such as 1,3; 2,4-dibenzylidenesorbitol.

Other additives that can be incorporated in the stabilized compositions are antiblocking agents, clarifiers, antiozonants, lubricants such as stearyl alcohol, fillers, carbon black, asbestos, kaolin, talc, glass fibers, pigments, optical brighteners, flameproofing agents and antistatic agents.

While the stabilizers of this invention may be conveniently incorporated by conventional techniques into polyolefins before the fabrication thereof into shaped articles, it is also possible to apply the instant stabilizers by a topical application to the finished articles. This is particularly useful with fiber applictions where the instant stabilizers are applied topically to the fibers, for example, by way of a spin finish during the melt spinning process.

The following examples are presented for the purpose of illustration only and are not to be construed to limit the nature of scope of the instant invention in any manner whatsoever.

EXAMPLE 1

N-Decyl-alpha-nonyl nitrone

To a solution of 29.8 grams of didecylamine in 120 ml of n-propanol is added sequentially 1.6 grams of sodium tungstate dihydrate and 14.3 grams of a 50% aqueous hydrogen peroxide solution at 5°-10° C. The reaction mixture is allowed to warm up to 40° C. and is maintained at that temperature for 20 hours. An additional 7.2 grams of 50% aqueous hydrogen peroxide solution is added to the solution at 40° C. After further stirring for another day, the reaction mixture is concentrated under reduced pressure. The residue is partitioned between chloroform and water. The combined organic extracts are washed with water and then dried over anhydrous sodium sulfate. Removal of the chloroform solvent leaves a crude product which is purified by recrystallization from heptane to afford the above-named compound as a white solid melting at 63°-65° C. in a yield of 9.8 grams.

Analysis: Calcd. for $C_{20}H_{41}NO$: C, 77.1; H, 13.3; N, 4.5. Found: C, 77.1; H, 13.7; N, 4.5.

EXAMPLE 2

N,N-Di(hydrogenated tallow)hydroxylamine

Into a solution of 100 grams (0.18 mol) of di(hydrogenated tallow)amine (494 eq. wt., 90% secondary amine) in 400 ml of n-butanol at 55° C. is added 8.6 ml (0.22 mol) of 70% aqueous hydrogen peroxide solution. The reaction is complete when all the hydrogen peroxide is consumed as determined by titration of an aliquot of the reaction mixture with potassium iodide/sulfuric acid/sodium thiosulfate.

The above-named product is isolated from the reaction mixture by filtration. The filter cake is washed with two 50 ml portions of n-butanol at 55° C.; then dried to give the desired product in a yield of 63 grams (68%) as a white solid melting at 93°-96° C.

EXAMPLE 3

Nitrone Derived from Di(hydrogenated tallow)hydroxylamine

To a solution of 3.5 grams of di(hydrogenated tallow)hydroxylamine, prepared as in Example 2, in 35 ml of toluene is added 2.8 ml of a 3.65 M tert-butyl hydroperoxide solution in toluene. The resulting solution is heated under reflux for 30 minutes. The reaction mixture is concentrated under reduced pressure. The residue is first purified by recrystallization from isopropanol and then by a second recrystallization from toluene.

The above titled nitrone is isolated as a white solid melting at 83°-85° C. in a yield of 1.5 grams.

Analysis: Calcd. for $C_{36}H_{73}NO$: C, 80,7; H, 13.7; N, 2.6. Found: C, 81.1; H, 14.2; N, 2.7.

EXAMPLE 4

Nitrone Derived from Di(hydrogenated tallow)amine

The above named compound is also prepared by the procedure described in Example 1 by the direct oxidation of the di(hydrogenated tallow)amine using 50% aqueous hydrogen peroxide and sodium tungstate.

EXAMPLE 5

N-Tert-butyl-alpha-phenyl Nitrone

Following the general procedure of Example 1, N-benzyl-N-tert-butylamine is oxidized using a solution of 3-chloroperoxybenzoic acid dissolved in methylene chloride to give N-tert-butyl-alpha-phenyl nitrone as a white solid melting at 70°-72° C. This is the nitrone described in Japanese Sho No. 59-11345.

Analysis: Calcd. for $C_{11}H_{15}NO$: C, 74.5; H, 8.5; N, 7.9. Found: C, 74.5; H, 8.6; N, 7.9.

EXAMPLE 6

N-Octadecyl-alpha-heptadecyl Nitrone

To a stirred suspension of 4.0 grams (7.4 mmol) of N,N-dioctadecylhydroxylamine and 0.13 gram (0.4 mmol) of sodium tungstate dihydrate in 35 ml of isopropyl alcohol is added 0.60 gram of 50% aqueous solution of hydrogen peroxide. The reaction mixture is heated for 30 minutes during which time it becomes homogeneous. A tlc analysis conducted on the reaction mixture (9:1, chloroform:ethyl acetate eluent) indicates that a small amount of starting material is still present.

To the reaction mixture at reflux temperature is then added an additional 0.20 gram of 50% aqueous hydrogen peroxide and heating is continued for another 30 minutes. The reaction mixture is then filtered while hot to remove the sodium tungstate catalyst.

The filtrate is cooled to 0° C. and is filtered to give 3.58 grams (91% yield) of a white solid melting at 93°-96.5° C.

Analysis: Calcd. for $C_{36}H_{73}NO$: C, 80.7; H, 13.7; N, 2.61. Found: C, 80.3; H, 13.9; N, 2.6.

EXAMPLE 7

Process Stabilization of Polypropylene at 500° F. (260° C.)

The base formulation comprises 100 parts of unstabilized polypropylene (Profax 6501, Himont) with 0.10 parts of calcium stearate. ,The test stabilizer is solvent blended onto the polypropylene from a solution in methylene chloride. After removal of the solvent by evaporation under reduced pressure, the stabilized resin formulation is extruded at 100 rpm from a 1 inch (2.54 cm) diameter extruder at 500° F. (260° C.).

After each of the first, third and fifth extrusions, resin pellets are compression molded into 125 mil (3.2 mm) thick plaques at 380° F. (193° C.) and specimen yellowness index (YI) is determined according to ASTM D-1925. Low YI values indicate less yellowing. Additionally, the melt flow rate (in grams/10 minutes) according to ASTM D-1238 is measured on the pellets after the first and fifth extrusions. The closer the melt flow rate after the fifth extrusion is to the melt flow rate after the first extrusion indicates superior process stabilization of the polypropylene.

| Stabilizer* | Stab. Conc. % by wt | Yellowness Index Color After Extrusion | | | Melt Flow Rate After Extrusion | |
|---|---|---|---|---|---|---|
| | | 1 | 3 | 5 | 1 | 5 |
| Base Formulation | — | 2.2 | 2.4 | 2.5 | 7.0 | 14.6 |
| AO A | 0.1 | 5.0 | 6.9 | 7.6 | 4.2 | 7.3 |
| AO A plus Nitrone of Example 1 | 0.1 0.05 | 2.4 | 3.6 | 5.4 | 3.4 | 6.0 |
| Nitrone of Example 3 | 0.05 | 2.6 | 4.0 | 6.0 | 3.5 | 6.1 |
| Nitrone of Example 5 | 0.05 | 6.6 | 8.9 | 10.7 | 4.1 | 6.8 |

*Base formulation contains 0.1% of calcium stearate
AO A is neopentanetetrayl tetrakis (3,5-di-tert-butyl-4-hy-droxyhydrocinnamate)

The instant nitrones of Examples 1 and 3 in the presence of calcium stearate and the phenolic antioxidant provide perceptibly better process stabilization protection to the polypropylene both in resistance to discoloration and in resistance to polymer degradation than does the phenolic antioxidant.

The prior art nitrone of Example 5 imparts additional color to the composition over the composition containing only the phenolic antioxidant. The instant nitrones are clearly superior to the nitrone disclosed in the prior art.

EXAMPLE 8

Process Stabilization of Polypropylene at 500° F. (260° C.)

The base formulation comprises 100 parts of unstabilized polypropylene (Profax 6501, Himont) with 0.10 parts of calcium stearate. The test stabilizer is solvent blended onto the polypropylene from a solution in methylene chloride. After removal of the solvent by evaporation under reduced pressure, the stabilized resin formulation is extruded at 100 rpm from a 1 inch (2.54 cm) diameter extruder at 500° F. (260° C.).

After each of the first, third and fifth extrusions, resin pellets are compression molded into 125 mil (3.2 mm) thick plaques at 380° F. (193° C.) and specimen yellowness index (YI) is determined according to ASTM D-1925. Low YI values indicate less yellowing. Additionally, the melt flow rate (in grams/10 minutes) according to ASTM D-1238 is measured on the pellets after the first and fifth extrusions. The closer the melt flow rate after the fifth extrusion is to the melt flow rate after the first extrusion indicates superior process stabilization of the polypropylene.

| Stabilizer* | Stab. Conc. % by wt | Yellowness Index Color After Extrusion | | | Melt Flow Rate After Extrusion | |
|---|---|---|---|---|---|---|
| | | 1 | 3 | 5 | 1 | 5 |
| Base Formulation | — | 2.2 | 2.4 | 2.5 | 7.0 | 14.6 |
| AO A | 0.1 | 5.0 | 6.9 | 7.6 | 4.2 | 7.3 |
| Nitrone of Example 1 | 0.1 | 1.8 | 3.3 | 4.5 | 3.4 | 6.5 |
| Nitrone of Example 3 | 0.1 | 2.1 | 3.1 | 3.2 | 3.6 | 6.2 |
| Nitrone of Example 5 | 0.1 | 2.5 | 3.0 | 3.8 | 4.2 | 7.8 |

*Base formulation contains 0.1% of calcium stearate
AO A is neopentanetetrayl tetrakis (3,5-di-tert-butyl-4-hy-droxyhydrocinnamate)

Each of the nitrones provides better resistance to discoloration than does the phenolic antioxidant. The prior art nitrone of Example 5 affords about the same level of process stabilization to the polypropylene composition as does the phenolic antioxidant.

The instant nitrones of Examples 1 and 3 are more effective than the prior art nitrone or the phenolic antioxidant in affording resistance to polymer degradation is measured by melt flow rate values.

EXAMPLE 9

Process Stabilization of Polypropylene at 500° F. (260° C.)

When, following the procedure of Example 8, an equivalent amount of a mixture of the N,N-di(hydrogenated tallow)hydroxylamine and N-octadecyl-alpha-heptadecyl nitrone is used as stabilizer in the polypropylene containing 0.1% of calcium stearate, excellent protection against discoloration and against polymer degradation during processing is obtained.

What is claimed is:

1. A long chain N-alkyl-alpha-alkyl nitrone compound of the formula

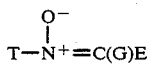

wherein
T is a straight or branched chain alkyl of 16 to 18 carbon atoms,
G is hydrogen, methyl or ethyl,
E is a straight or branched chain alkyl of 13 to 17 carbon atoms, and
where the sum of the carbon atoms in G plus E is equal to 15 to 17.

2. A compound according to claim 1 where T is hexadecyl, heptadecyl or octadecyl or is the alkyl mixture found in hydrogenated tallow amine.

3. A compound according to claim 2 where T is the alkyl mixture found in hydrogenated tallow amine.

4. A compound according to claim 1 where G is hydrogen or methyl.

5. A compound according to claim 4 where G is hydrogen.

6. A compound according to claim 1 where E is tridecyl, pentadecyl, hexadecyl, heptadecyl or is the alkyl mixture found in hydrogenated tallow amine with one less carbon atom per alkyl group.

7. A compound according to claim 6 where E is the alkyl mixture found in hydrogenated tallow amine with one less carbon atom per alkyl group.

8. A nitrone according to claim 1 wherein T is the alkyl mixture found in hydrogenated tallow amine, G is hydrogen, and E is the alkyl mixture found in hydrogenated tallow amine with one less carbon atom per alkyl group.

9. The compound according to claim 1 which is N-octa-decyl-alpha-heptadecyl nitrone.

10. A stabilized composition which comprises
   (a) a saturated polyolefin or mixture thereof, and
   (b) a stabilizing amount of a long chain N-alkyl-alpha-alkyl nitrone of the formula

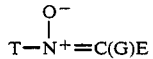

wherein

T is a straight or branched chain alkyl of 16 to 18 carbon atoms,

G is hydrogen, methyl or ethyl,

E is a straight or branched chain alkyl of 13 to 17 carbon atoms, and where the sum of the carbon atoms in G plus E is equal to 15 to 17.

11. A composition according to claim 10 wherein component (a) is a polyolefin which is a homopolymer or copolymer of an alpha-olefin.

12. A composition according to claim 11 wherein the polyolefin is selected from the group consisting of polypropylene, low density polyethylene, medium density polyethylene, high density polyethylene, linear low density polyethylene, poly(butene-1), ethylene/vinyl acetate copolymer, ethylene/propylene copolymer and copolymers of ethylene or of propylene with other alpha-olefins.

13. A composition according to claim 12 wherein the polyolefin is polypropylene, high density polyethylene, ethylene/propylene copolymer or a copolymer of ethylene or of propylene with another alpha-olefin.

14. A composition according to claim 10 where in component (b) T is hexadecyl, heptadecyl or octadecyl or is the alkyl mixture found in hydrogenated tallow amine.

15. A composition according to claim 14 wherein T is the alkyl mixture found in hydrogenated tallow amine.

16. A composition according to claim 10 where in component (b) G is hydrogen or methyl.

17. A composition according to claim 16 wherein G is hydrogen.

18. A composition according to claim 10 where in component (c) E is tridecyl, pentadecyl, hexadecyl heptadecyl or is the alkyl mixture found in hydrogenated tallow amine with one less carbon atom per alkyl group.

19. A composition according to claim 18 wherein E is the alkyl mixture found in hydrogenated tallow amine with one less carbon atom per alkyl group.

20. A composition according to claim 10 which additionally contains a stabilizing amount of a stabilizer or mixture of stabilizers selected from the group consisting of the phenolic antioxidants, the hindered amine light stabilizers, the ultraviolet light absorbers, the organic phosphorus compounds, the alkaline metal salts of fatty acids, the thiosynergists and the hydroxylamines.

21. A composition according to claim 20 wherein the additional stabilizer is
(c) a stabilizing amount of an alkaline metal salt of a fatty acid or mixture thereof.

22. A composition according to claim 21 wherein component (c) is calcium stearate, zinc stearate, magnesium behenate, sodium ricinoleate or potassium palmitate.

23. A composition according to claim 22 wherein component (c) is calcium stearate or zinc stearate.

24. A composition according to claim 20 wherein the additional stabilizer is
(d) a stabilizing amount of a phenolic antioxidant or mixture thereof.

25. A composition according to claim 24 wherein the phenolic antioxidant of component (d) is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxy-benzylphosphonate, 1,3,5-tris-(3,5,-di-tert-butyl-4-hydroxybenzyl)isocyanurate, thiodiethylene bis(3,5-di-tert-butyl-4-hydroxyhydrocinnamate), 1,3,5-trimethyl-2,4,6-tris (3,5-di-tert-butyl-4-hydroxybenzyl)-benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl) isocyanurate, 1,1,3-tris-(2-methyl-4-hydroxy-5-tert-butylphenyl)butane, 1,3,5-tris-[2-(3,5-di-tert-butyl-4-hydroxyhydrocinnamoyloxy)-ethyl] isocyanurate, 3,5-di-(3,5-di-tert-butyl-4-hydroxybenzyl)-mesitol, hexamethylene bis(3,5-di-tert-butyl-4-hydroxyhydrocinnamate),1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl-3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-tert-butyl-4-hydroxyhydroxo-cinnamoyloxy)ethyl]-oxamide.

26. A composition according to claim 25 wherein the phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)-benzene, 1,3,5-tris-(3,5-di-tert-butyl-4-hydroxybenzyl) isocyanurate, 2,6-di-tert-butyl-p-cresol or 2,2'-ethylidene-bis-(4,6-di-tert-butylphenol).

27. A composition according to claim 20 wherein the additional stabilizer is
(e) a stabilizing amount of an N,N-dialkylhydroxylamine where alkyl is of 8 to 18 carbon atoms.

28. A composition according to claim 27 wherein component (e) is N,N-di(hydrogenated tallow)hydroxylamine and component (b) is N-octadecyl-alpha-heptadecyl nitrone.

* * * * *